(12) United States Patent
Bach et al.

(10) Patent No.: US 7,160,730 B2
(45) Date of Patent: Jan. 9, 2007

(54) METHOD AND APPARATUS FOR CELL SORTING

(76) Inventors: David T. Bach, 3211 Governor Johnson Ct., Ellicott City, MD (US) 21043; Muniswamappa Anjanappa, 2004 Eliza Dorsey Ln., Ellicott City, MD (US) 21042

( * ) Notice: Subject to any disclaimer, the term of this patent is extended or adjusted under 35 U.S.C. 154(b) by 271 days.

(21) Appl. No.: 10/688,331

(22) Filed: Oct. 17, 2003

(65) Prior Publication Data

US 2004/0077033 A1 Apr. 22, 2004

Related U.S. Application Data

(60) Provisional application No. 60/420,351, filed on Oct. 21, 2002.

(51) Int. Cl.
*G01N 33/48* (2006.01)
*C12M 1/34* (2006.01)

(52) U.S. Cl. .................. 436/63; 436/150; 436/164; 436/172; 436/177; 436/180; 422/68.1; 422/73; 422/82.05; 422/82.08; 422/82.09; 422/101; 435/29; 435/287.1; 435/287.3

(58) Field of Classification Search .............. 436/63, 436/52, 164, 172, 177, 180, 149, 150; 422/68.1, 422/73, 82.05, 82.08, 82.09, 100, 101; 435/4, 435/29, 287.1, 287.3, 40.5
See application file for complete search history.

(56) References Cited

U.S. PATENT DOCUMENTS

| | | | | |
|---|---|---|---|---|
| 3,790,760 A | * | 2/1974 | Stiller | ................... 377/10 |
| 3,827,555 A | * | 8/1974 | Kamentsky et al. | ........ 209/546 |
| 4,158,368 A | * | 6/1979 | Clark | ................... 137/487.5 |
| 4,756,427 A | * | 7/1988 | Gohde et al. | ............... 209/3.1 |
| 5,837,200 A | * | 11/1998 | Diessel et al. | ............... 422/73 |
| 6,540,895 B1 | * | 4/2003 | Spence et al. | ............. 204/450 |
| 6,778,724 B1 | * | 8/2004 | Wang et al. | ................. 385/16 |
| 2003/0027225 A1 | * | 2/2003 | Wada et al. | ............. 435/7.21 |

OTHER PUBLICATIONS

Copending U.S. Appl. Nos. 10/690,766, 10/965,287, 10/689,480, 10/965,289.

"A Theoretical and Experimental Study of Magnetostrictive Mini-Actuators" Anjanappa et al, 1994.

* cited by examiner

*Primary Examiner*—Maureen M. Wallenhorst
(74) *Attorney, Agent, or Firm*—Ober / Kaler; Royal W. Craig

(57) ABSTRACT

A cell sorter system that includes a precision pump that causes fluid containing cells to enter an inlet port where the fluid is exposed to source light of one or more wavelengths and where cells scatter light or produce fluorescence by known means, and the scattered light and/or fluorescence is used to detect the presence and position of desired cells. The fluid is passed into a select gate that can be magnetostrictive where it is cause to exit one of a plurality of ports, at least one of these ports receiving the desired cells. A controller controls the precision pump, the detection system, and the select gate so that cells are selected from the fluid. An optional vacuum system can be used to pull fluid or cells out of the selected exit port.

19 Claims, 3 Drawing Sheets

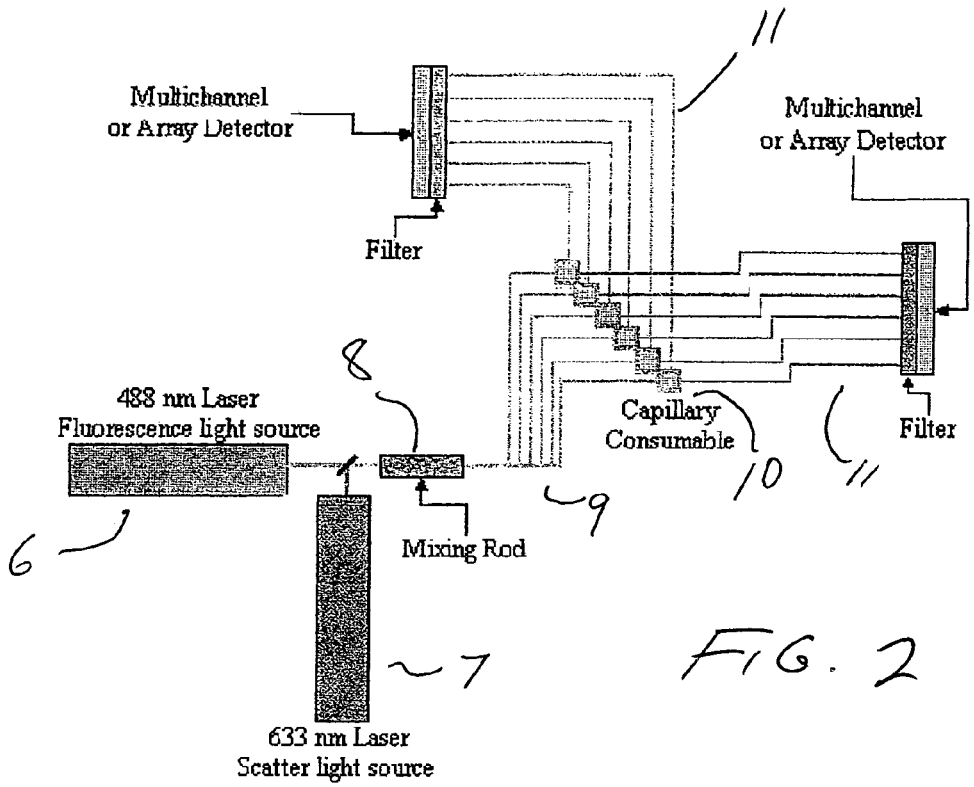
FIG. 2
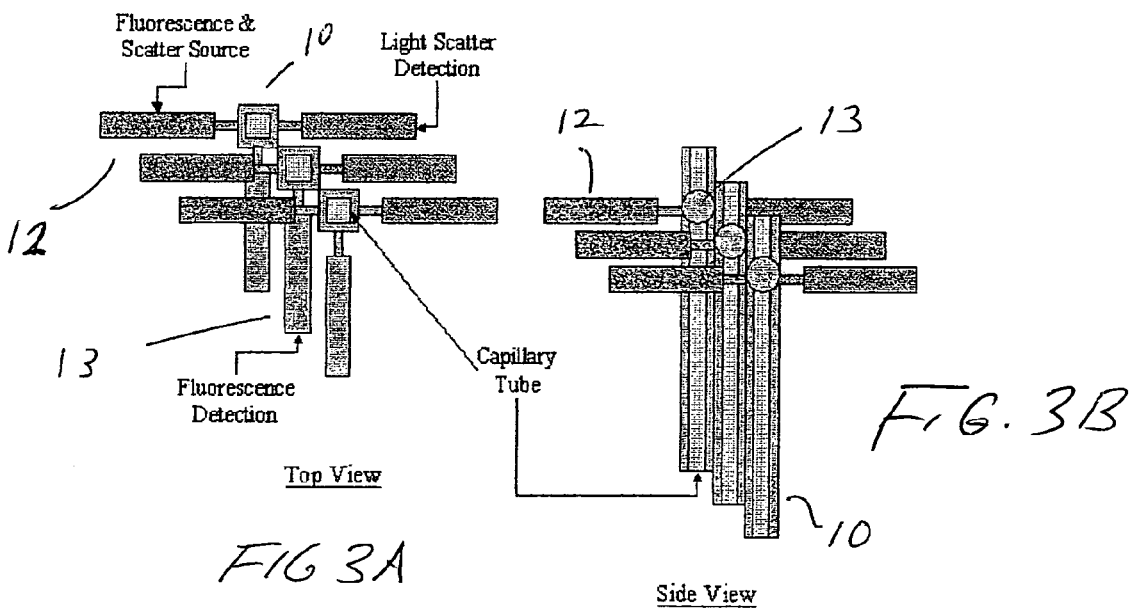
FIG. 3A
FIG. 3B

METHOD AND APPARATUS FOR CELL SORTING

This application is related to and claims priority from U.S. provisional patent application No. 60/420,351 filed Oct. 21, 2002 and hereby incorporates that application by reference.

BACKGROUND

1. Field of the Invention

The present invention relates generally to the field of biological and medical instruments and more particularly to a method and apparatus for automatic cell sorting using gating technology.

2. Description of the Prior Art

There is a large demand for cost effective cell sorting of stem and other cell types. Sorted isolated cell populations are used for transplantation into myeloablated cancer patients. There are currently about 100,000 such transplantations a year in the US. Cell sorting ideally needs to take place in a closed consumable container where hematopoeitic stem and progenitor cell populations are sorted from peripheral blood, umbilical cord blood, and bone marrow. However, current cell sorters require constant parameter adjustments, use open flow sorting technology which is susceptible to contamination and these sorters can cost in excess of $250,000.

Automated cell sorting techniques are becoming indispensable for both research and clinical applications. Typical prior art instruments interrogate the physical and chemical properties of cells followed by a physical separation of cells of interest at high speeds. The interrogations of each cell are done using optical techniques such as fluorescence followed by separation of the cells of interest using electrostatic or other physical separation methods. Conventional cell sorters utilize a single channel that operates at sorter rates of up to 60,000 cells per second. The sorting is done using an open fluid flow system that creates an aerosol environment.

There are several drawbacks to the prior art techniques: 1) the sorting rates cannot be much increased due to shear and pressure forces that damage the cells; 2) because separation takes place in an open fluid flow environment, there is a high potential for contamination; 3) the cost of current sorters is high.

What is badly needed is a cell sorter that operates in a closed flow environment (completely contained and isolated fluid system)that has intrinsic capability for very much faster sorting rates.

SUMMARY OF THE INVENTION

The present invention relates to a cell sorter system for sorting desired cells from undesired matter which includes a precision pump for pumping cell-containing fluid into a detection and gating region and controlling positions of the cells in the detection and gating region; an optical detection system for determining when a desired cell is in a predetermined position in the detection and gating region; a select gate that can be magnetostrictive controlled, or otherwise controlled, that causes a desired cell to pass through a cell exit port and waste material to pass through a waste port according to an applied control signal or a magnetic field; and an optional vacuum system to cause the desired cell and/or waste to exit the correct ports.

The select gate, pump and detection system can be controlled by a microprocessor. Optical detection can be based on fluorescence, scattered light or both. Both methods can be used simultaneously.

A magnetostrictive device is made from material that changes shape under an applied magnetic field. A magnetostrictive gate can be made from a monolithic or composite rod of magnetostrictive material that causes a valve to select a fluid channel between two or more ports (or an off-on situation using only one port). The rod can have any cross-section; however, cylindrical is preferred (Note: other structures besides rods will work). The control system can apply a magnetic field when flow through one of the ports is desired (for example, when a desired cell is in position). In the absence of any magnetic field, flow can take place through another port such as a waste port.

DESCRIPTION OF THE DRAWINGS

FIG. 2 shows a layout diagram of an optical detection system.

FIG. 3A shows a detail of optical coupling in and out of capillary tubes.

FIG. 3B is a side view of FIG. 3A.

Several figures and drawings have been presented to better explain the present invention. The present invention is not limited to the embodiments or scope of the drawings.

DESCRIPTION OF THE INVENTION

Figure 1:
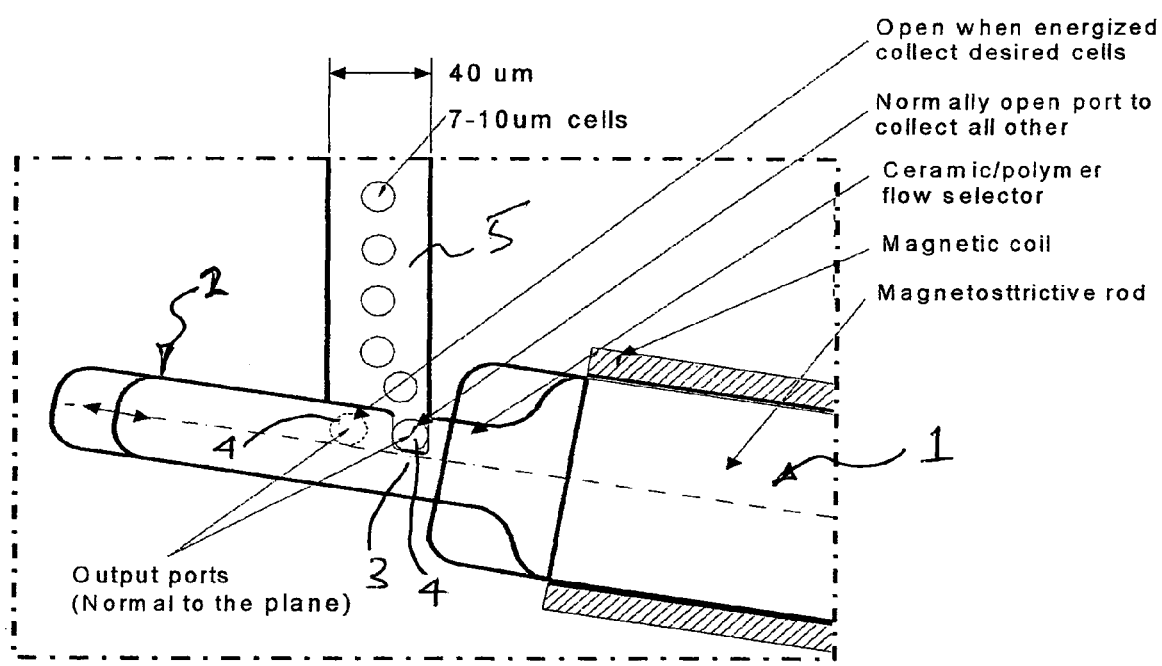
FIG. 1 shows a magnetostrictive capillary gating mechanism.

The present invention relates to the use of magnetostrictive technology or other technology to create a cell sorter with a magnetostrictive gating mechanism (or any other high speed gating method). In a preferred embodiment, this gating mechanism utilizes a magnetostrictive rod coupled to a flow port selector component. FIG. 1 shows a magnetostrictive capillary gating mechanism. A magnetostrictive mini-rod 1 is mechanically connected to a ceramic or similar material flow selector 2 with a slot 3 that uncovers one of two, or more, output ports 4 depending upon whether the mini-rod 1 is excited or un-excited by a magnetic field.

The mini-rod 1 is excited with a magnetic field that originates outside the capillary flow region. There needs to be no physical contact between the magnetic field generation means and the flow region. The mini-rod 1, by virtue of its magnetostriction property, physically expands when excited by an externally applied magnetic field. The flow selector 2 thus forms a valve between the ports 4 that can be very quickly and efficiently controlled with an external magnetic field.

The gating system of FIG. 1 can be exercised when a selected cell is in the correct position at the gate. Both ports 4(or multiple ports) can have individual vacuum sources coupled to them so that the opening of one of the ports allows the cells of interest to be moved (removed) by a combination of suction and flow dynamics. Once the cells of interest are removed, the magnetic field can also be removed, and the gating port allowed to re-align with the other (or one of the other) ports for normal waste flow exit.

Fluid is caused to flow into the system from a precision fluid pump into an input channel or capillary 5 that can be around 40 micrometers in diameter. The capillary 5 ends at the selection device 2. FIG. 1 shows the device in the normal position where a cell has not been selected for removal. The speed of the fluid flow from the pump can normally be high, and when a cell needs to be removed, the pump speed can be reduced and carefully synchronized to the selection port.

When a cell needs to be removed, the fluid pump can be stopped, the gate moved to the remove position, the pump moved for one cell removal, and then the gate moved back to its normal closed position. A typical magnetostrictive rod is capable of moving around 1000 parts per million or around 1 micron per millimeter. For a movement of 25–30 microns, a rod of this type would need to be around 25–30 mm long. Any rod of any material that can expand is within the scope of the present invention. The gating device shown in FIG. 1, using a mangetostrictive rod, is capable of operating at speeds up to 10,000 Hz.

The system shown in FIG. 1 is coupled fluid-wise to a precision dispensing pump. The pump system should be capable of making precise micro-displacements of at least 0.5 micron resolution to obtain maximum accuracy. The pump system is capable of removing large volumes of aphaeresis material, and then slowing feeding the material to the input capillary channel or channels 5. The fluid is generally moved to the capillary tube in discrete movements that are usually synchronized to an optical detection system and the cell gating system shown in FIG. 1. Continuous flow systems are within the scope of the present invention.

The overall cell sorter system couples the action of a precision pump, an optical detection system and a sorting gate mechanism such as is shown in FIG. 1. FIG. 2 shows an embodiment of an optical detection system that is could be used with the present invention. An argon 488 nm laser 6 acts as a fluorescence source while a helium neon 633 nm laser 7 acts as a light scatter source. The two lasers are coupled into a mixing rod 8 that is used to combine the source wavelengths and effectively couple light into fibers 9. The light fibers 9 are used to bring light into capillary cells 10. Pairs of other fibers 11 are used to couple fluorescence and light scatter from each capillary cell into multi-channel array detectors 12. The multi-channel array detectors 12 can contain photo-multipliers or diode arrays or any other light detection means. Any other type of optical system or combination of wavelengths is within the scope of the present invention.

The fiber optics 11 can be positioned as shown in FIGS. 3A and 3B where each capillary is positioned so that the optics for the source and detector are 180 degrees apart. Fluorescence detection can have its fibers one above another as shown in FIGS. 3A and 3B. The capillary detection modules can be round or square and can use optical refractive index matching fluids for coupling into the output fibers (or lens/fibers). FIGS. 3A and 3B show the capillary tubes 10 from a top view (FIG. 3A) and a side view (FIG. 3B). A Fluorescence and light scatter source 12 feeds the light of two different wavelengths into the capillaries 10. Fluorescence detection 13 and light scatter detection 14 can be positioned 90 degrees apart as shown in FIGS. 3A and 3B. The embodiments shown in FIGS. 3A and 3B are representative of the types that can be used with the present invention. The present invention includes many other embodiments of optical detection.

When either a fluorescence or light scatter signal (or both) indicates a cell to be sorted is in position, the pump control electronics keeps track of the time shift necessary so that the cells are properly presented to the gating mechanism. The gating mechanism can be exercised when the selected cell is in exactly the correct position. Both ports under the gating mechanism can have a vacuum source coupled to them. The opening of the proper port causes the selected cell to exit (be removed) through the correct channel. One exit channel could be for selected cells and the other for all else. Multiple channels (more than two) are within the scope of the present invention and can lead to more sophisticated sorting based on various cell properties.

When a selected cell is in position in the capillary, the control electronics either applies the external magnetic field, or not, depending upon which exit port is desired. Once the magnetic field is removed (if it had been applied), the gate re-aligns itself to the normal position or non-selected (waste) port. The speed of fluid flow from the pump can be high as previously discussed. When a cell needs to be removed, the flow speed can be reduced and carefully synchronized to the gate. Continuous flow systems are within the scope of the present invention.

Figure 4A:
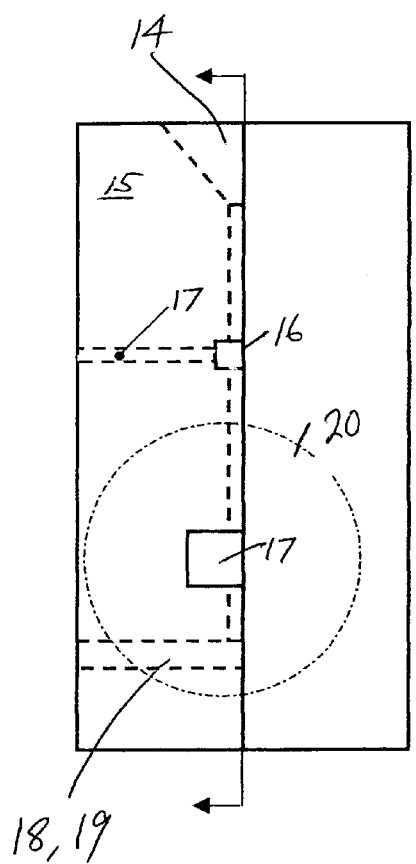
FIG. 4A is a view of a fluidic micro-channel module.
Figure 4B:
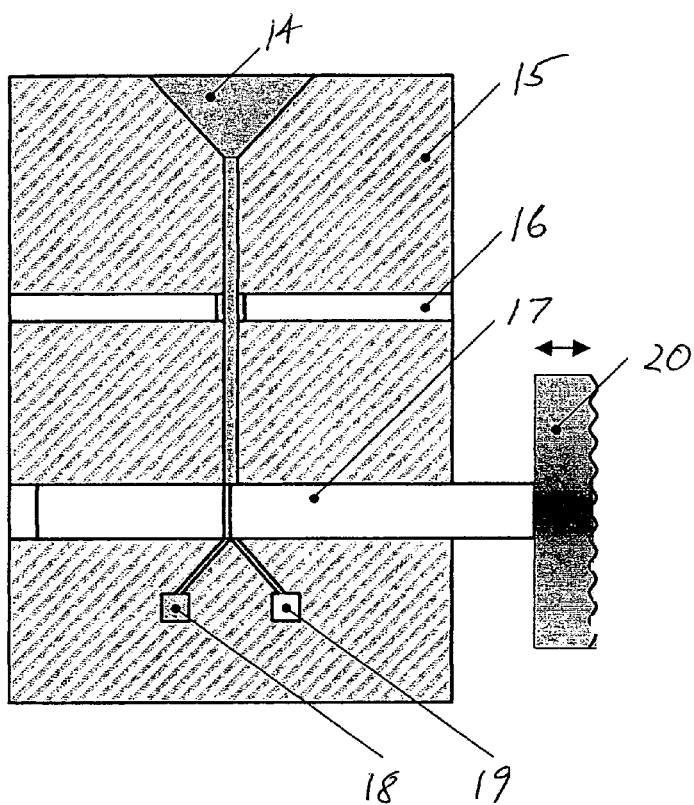
FIG. 4B is a sectional view of the module from FIG. 4A.

FIGS. 4A and 4B show an embodiment of a fluidic micro-channel module that can be laser machined with an Eximer laser on a ceramic or polymer (or any other suitable material) substrate. A fluid inlet port 14 can be part of a laser machined micro-channel plate 15. The fluid inlet port 14 leads to fluorescence and scattered light channel 16 and on to a flow selector component or gate 17 and on to an cell collector port 18 and a waste port 19. A magnetotrictive rod 20 is shown attached to the flow selector 17 such that when it experiences an applied magnetic field, it changes the flow from the waste port 19 to the cell collector port 18. As stated before, the control electronics causes the magnetic field to be applied (or not applied) to choose one of the ports just when the cell is in the correct position. The sensor for the cell position can be the fluorescence or scattered light detectors external to the module shown in FIGS. 4A and 4B.

The present invention thus couples a precision pump, an optical cell detection system and a control channel into a closed system that can move a cell into position to be identified, identify it and make a sort decision, move the selected cell to the control gate (if not already in position), set the control gate, and pull the selected cell out into a proper exit port. The present invention can be run in a pulsed (or discrete motion) mode, or it can be run with continuous flow and hence continuous cell motion. Cells are identified and classified by the optical detection system according to optical properties that are either intrinsic or can be given to the desired cells through methods well-known in the art.

The present invention allows cells to be sorted by using a dynamic gate that can be constructed using magnetostrictive or other technology to create a small capillary valve. The valve can be switched from one state to another by the application of a magnetic field. The valve can be constructed where two (or more) ports are very close together so that as one port closes, the other is opening, or it can be constructed with ports further apart so that there is a period of time when both ports are blocked. The valve system can be part of a single or multiple capillary block. Such a block can be micro-machined using laser technology. The fluid flow through the present invention can be pulsed or continuous. Cells and other material can be sucked out of ports using an optional vacuum system on each port. Cell detection can be accomplished using either fluorescence or scattered light, or both simultaneously. The system can be controlled by a single or by multiple microprocessors.

The present invention has been described by written descriptions and figures. A person skilled in the art will realize that many changes and variations can be made that are still within the scope of the present invention.

We claim:

1. A cell sorter comprising:
   a pulsed-mode precision microdisplacement pump coupled to a fluid inlet port, said pump causing fluid containing desired cells to enter said inlet port and stopping fluid flow when a particular cell is at a predetermined position;

a cell detection system fluidly coupled to said inlet port, said cell detection system determining whether a particular cell stopped at said predetermined position is a desired cell;

a sorting gate including a magnetostrictive actuator rod, said sorting gate having at least two states fluidly coupled to said cell detection system, said sorting gate allowing said desired cell to exit a cell collection port and allowing waste to exit a waste port in accordance with the determination of said cell detection system;

a control unit connected to said pump, said cell detection system and said sorting gate for synchronizing discrete fluid microdisplacements by said pump with said cell detection system and magnetostrictive actuator of said sorting gate, said control unit processing information from said cell detection system and causing said pump to stop cells in said fluid at said predetermined position, causing said sorting gate to select said cell collection port when a cell is a desired cell, and then starting said pump to cause said desired cell to exit said cell collection port.

2. The cell sorter of claim 1 wherein said cell detection system is optical.

3. The cell sorter of claim 2 wherein said cell detection system uses fluorescence.

4. The cell sorter of claim 2 wherein said cell detection system uses scattered light.

5. The cell sorter of claim 2 wherein said cell detection system uses both fluorescence and scattered light.

6. The cell sorter of claim 5 wherein a fluorescence and scattered light determination is made simultaneously.

7. The cell sorter of claim 1 further comprising said control unit pulsing said pump to pump an amount of fluid sufficient to move said desired cell into said cell collection port after said sorting gate has selected said cell collection port.

8. A cell sorter system for sorting desired cells from undesired matter comprising:

a pulsed-mode precision microdisplacement pump coupled to a capillary for causing fluid containing cells to enter said capillary;

an optical detection system in proximity to a predetermined position in said capillary; and a magnetostrictive gate switching between a cell exit port and a waste port in said capillary;

said pulsed-mode pump pumping cell-containing fluid into the capillary and controlling positions of cells in said capillary by stopping flow of said fluid at said predetermined position in said capillary;

said optical detection system determining whether an individual cell is a desired cell while stopped at said predetermined position; and said magnetostrictive gate switching flow from said waste port to said cell exit port when said pump stops allowing the desired cell to pass through said cell exit port by pulsing the pump to move said cell through said cell exit port.

9. The cell sorter system of claim 8 further comprising a means for applying a magnetic field to said magnetostrictive gate, whereby said magnetostrictive gate switches from said waste port to said cell exit port.

10. The cell sorter system of claim 8 wherein said optical detection system uses fluorescence.

11. The cell sorter of claim 8 wherein said optical detection system uses scattered light.

12. The cell sorter system of claim 8 wherein said optical detection system uses both fluorescence and scattered light simultaneously.

13. The cell sorter system of claim 8 wherein said optical detection system includes a photomultiplier.

14. The cell sorter system of claim 8 wherein said optical system includes a diode array.

15. A method for sorting cells comprising:

causing fluid containing cells to enter an inlet port of a capillary by pulsing a precision microdisplacement pump, thereby incrementally pumping said fluid;

stopping said precision pump so as to cause said fluid to stop an optical detection region in the capillary where said fluid is exposed to light of at least one predetermined wavelength, wherein scattered light or fluorescence from said cells is used to choose a particular desired cell;

pulsing said precision pump to position said particular desired cell in a predetermined position in proximity to a closed cell exit port;

applying a magnetic field to a magnetostrictive gate causing said magnetostrictive gate to open said cell exit port;

pulsing said precision pump to cause said particular desired cell to pass through said cell exit port;

removing said magnetic field from said magnetostrictive gate causing said magnetostrictive gate to close said cell exit port; and drawing said particular desired cell from said exit port.

16. The method of claim 15 wherein said magnetostrictive gate contains a magnetostrictive rod.

17. The method of claim 16 wherein said magnetostrictive rod changes length in an applied magnetic field.

18. The method of claim 15 wherein said light is directed into said optical detection region by fiber optics.

19. The method of claim 15 wherein the step of drawing said particular desired cell from said exit port is performed using a vacuum.

* * * * *